US006138671A

United States Patent [19]

Noakes et al.

[11] Patent Number: 6,138,671

[45] Date of Patent: Oct. 31, 2000

[54] ELECTROSTATIC SPRAYING OF PARTICULATE MATERIAL

[75] Inventors: Timothy James Noakes, Nr Mold Clwyd; Michale Leslie Green, Clwyd; Andrew Jefferies, Nr Mold Clwyd; Maurice Joseph Prendergast, Runcorn, all of United Kingdom

[73] Assignee: The Procter & Gamble Company, Cincinnati, Ohio

[21] Appl. No.: 08/809,984

[22] PCT Filed: Sep. 19, 1995

[86] PCT No.: PCT/GB95/02218

§ 371 Date: Apr. 2, 1997

§ 102(e) Date: Apr. 2, 1997

[87] PCT Pub. No.: WO96/10459

PCT Pub. Date: Apr. 11, 1996

[30] Foreign Application Priority Data

| | | | |
|---|---|---|---|
| Oct. 4, 1994 | [GB] | United Kingdom | 9419988 |
| Oct. 11, 1994 | [GB] | United Kingdom | 9420511 |
| Jun. 7, 1995 | [GB] | United Kingdom | 9511514 |

[51] Int. Cl.[7] .................. A61M 15/02

[52] U.S. Cl. .................. 128/202.25; 128/203.15

[58] Field of Search .................. 128/202.25, 203.15; 239/690, 691

[56] References Cited

U.S. PATENT DOCUMENTS

| | | | |
|---|---|---|---|
| 2,742,185 | 4/1956 | Landry | 222/1 |
| 2,748,018 | 5/1956 | Miller | 427/474 |
| 4,331,298 | 5/1982 | Bentley et al. | 239/690 |
| 5,121,884 | 6/1992 | Noakes | 239/691 |
| 5,184,778 | 2/1993 | Noakes | 239/691 |
| 5,222,664 | 6/1993 | Noakes et al. | 239/691 |
| 5,267,555 | 12/1993 | Pajalich | 128/205.25 |
| 5,405,090 | 4/1995 | Greene et al. | 239/690 |
| 5,505,195 | 4/1996 | Wolf et al. | 128/203.15 |
| 5,642,727 | 7/1997 | Datta et al. | 128/202.25 |
| 5,645,051 | 7/1997 | Schultz et al. | 128/203.15 |
| 5,669,973 | 9/1997 | Pletcher | 128/203.15 |
| 5,779,162 | 7/1998 | Noakes et al. | 239/690.1 |
| 5,857,456 | 1/1999 | Sun et al. | 128/203.15 |
| 5,871,010 | 2/1999 | Datta et al. | 128/203.15 |
| 5,875,776 | 3/1999 | Vaghefi | 128/203.15 |

FOREIGN PATENT DOCUMENTS

| | | |
|---|---|---|
| 0 044 038 | 1/1982 | European Pat. Off. . |
| 0 467 172 | 1/1992 | European Pat. Off. . |
| 0 516 510 | 12/1992 | European Pat. Off. . |
| 0 634 184 | 1/1995 | European Pat. Off. . |
| 1 081 124 | 12/1954 | France . |
| 1 440 170 | 4/1966 | France . |
| 1 519 092 | 3/1968 | France . |
| 2 381 570 | 9/1978 | France . |
| 2 413 938 | 8/1979 | France . |
| 2 010 126 | 6/1979 | United Kingdom . |
| 92 05824 | 4/1992 | WIPO . |
| 94 13063 | 6/1994 | WIPO . |
| 94 19042 | 9/1994 | WIPO . |

*Primary Examiner*—Aaron J. Lewis
*Attorney, Agent, or Firm*—Leonard W. Lewis

[57] ABSTRACT

A method and device (20) for spraying particulate materials in which a high voltage is applied to a mass of the particulate material so as to cause particles to issue from the mass. High voltage from a source (16) is applied to a mass of material (36) stored in a container. A surface of the mass (36) is exposed to the surroundings and the applied voltage is conducted through the bulk material to particles located at the exposed surface which are thereby projected as an electrically charged spray from the mass under the influence of the electric field substantially without any accompanying corona discharge.

16 Claims, 7 Drawing Sheets

ELECTROSTATIC SPRAYING OF PARTICULATE MATERIAL

This invention relates to electrostatic spraying.

There are a wide variety of methods available for effecting the dispensing of liquid-based materials. For instance, aerosol-type dispensers are in widespread use. Such dispensers are particularly convenient for dispensing personal care and personal hygiene formulations (eg perfumes, deodorants, cosmetics etc). Often in such applications, the active ingredient is in fact a solid material suspended or otherwise dispersed in a suitable liquid carrier to aid dispensing.

According to one aspect of the present invention there is provided a method of spraying particulate materials comprising applying a high voltage to a mass of the material in such a way as to electrically charge particles of the material and thereby effect propulsion of the particles away from said mass.

According to a second aspect of the present invention there is provided a method of spraying particulate materials comprising applying a high voltage to a mass of the material in such a way as to electrically charge particles of the material present at and/or in the vicinity of a surface or surfaces of the mass and and thereby generate an electric field by means of which the particles are caused to issue from such surface(s).

A feature of the invention resides in the absence of any liquid vehicle for suspension of the particulate material. Also high voltage is applied to the mass of particulate material prior to issue of particles from the mass.

The use of electrostatic fields in the spraying of particulate materials is known per se. For instance, as discussed in international Patent Application No. WO 94/19042 (Balachandran et al), it is known that the site of deposition within the respiratory tract of an inhalable substance can be influenced by the level of electrostatic charge on the particles of the inhalable substance. International Patent Application No. WO 94/19042 discloses a device in which the substance to be administered is dispensed in the form of inhalable particles (aerosol liquids or powder) into a passageway defined by a mouthpiece of the device and an arrangement of electrodes within the passageway is used to impact electrostatic charge to the particles so dispensed. In this way, the electrostatic charge characteristically imparted to particles on being dispensed from a particular type of dispensing means can be modified in a controlled manner as they pass through a charging region established by the electrode arrangement. Such modification is stated to encompass increases, reductions, reversal and neutralisation of the level of electrostatic charge on the particles.

With such an arrangement, it is difficult to secure a uniform level of electrostatic charge on the particles since the particles are dispersed into the inhaled airstream and passed through the electric field developed by the electrodes. Particles at different locations in the airstream therefore tend to receive difficult levels of electrostatic charge resulting in particles with a wide spectrum of electrostatic charge.

Also electrostatic spraying is used in coating articles with plastics material, the material initially being sprayed onto the article as a relatively thick layer and then consolidated to form a continuous layer by heating. The particulate material is fluidised and caused to flow by means of an air supply and is electrically charged by traversing a corona discharge electrode after being fluidised. In such coating techniques, the particulate material used has a high volume resistivity (typically $10^{14}$ ohm.cm and higher) and is not capable of being sprayed if voltage is applied to a mass of such material, ie since conduction of the applied voltage and charge leakage through the mass is largely prevented by the highly insulating nature of the material. Non-conduction of the charge is highly desirable since such spraying techniques are usually required to produce relatively thick adherent, coatings of material and the non-conduction of charge (ie lack of charge dissipation) is an important factor in ensuring that the material adheres to the target for the significant time period between spraying and subsequent heating and consolidation of the deposited particles.

In contrast, in the method of the present invention, the particulate material will tend to be of lower resistivity than used in the article coating methods just referred to in order that the particles can be charged by leakage of charge through the mass (rather than by means of a corona discharge). The ability of the particulate material to adhere by means of electrical forces will tend to be lower but, in general, the thickness of the layer to be deposited will tend to be substantially less and, where gravity may be a factor, in terms of adherence reliance is placed on the dampness or tackiness of the surface on to which the particulate material is sprayed. Also, in practising the methods of the present invention, it is unnecessary to produce a flow of gaseous fluid to effect transport of the particulate material. Instead the electric field is instrumental in propelling the particles.

As mentioned above, because of the lower resistivity employed in practising the present invention, adherence to surfaces by virtue of the electrical forces created tends to be reduced since charge leakage or dissipation can occur. The reduced adherence may be compensated for if the surface to be sprayed is damp or tacky. In some cases, the retention of the sprayed particulate material may be assisted by application of some form of adherence promoting agent to the surface to be sprayed and/or to the particulate material.

The mass of particulate material may be contained within a receptacle having a discharge outlet at which a surface of the mass is exposed at least during spraying.

The applied voltage may be positive or negative (positive voltages being preferred) and is typically in the range of 3 to 40 kV, usually less than 30 kV, eg 3 to 25 kV. An important feature of the invention is that the voltage is selected with the aim of preventing or minimising corona discharge. Thus, if the device is put into its operational state in the absence of the particulate material, the voltage selected is such that, without said mass present, there is substantially no corona discharge from the device. In the present invention, corona discharge is considered undesirable in contrast with the prior art where corona discharge is important.

In some instances, it may be desirable to use a high voltage generator producing an output which alternates between positive and negative polarities, for instance for shock suppression purposes or to allow the spraying of targets which are otherwise difficult to spray electrostatically (for example, hair—especially dry fine hair) as disclosed in our prior EP-A-468735 and 468736 and PCT-A-WO94/13063, the disclosures of which are incorporated herein where the context admits. Other features of our prior EP-A-120633, 441501, 482814, 486198, 503766 and 607182 may be employed in practising the present invention and the disclosures of these patent specifications are also incorporated herein where the context admits.

The high voltage generator may be of the type disclosed in EP-A-163390. However, voltage generators of this form are expensive to manufacture and are relatively bulky especially for use in electrostatic spraying devices required to be compact in size, eg sprayers for cosmetics, perfumes and medical and pseudo-medical formulations such as ocular, oral and nasal formulations and skin treatment agents. Moreover, the battery pack required for power supply must be accommodated within the housing of the sprayer and frequent battery replacement or recharging is necessary.

Accordingly in the present invention the voltage generator may be one comprising a large array of voltage producing elements interconnected to produce a high voltage.

Preferably the generator is a solid state device comprising hundreds or even thousands of individual voltage producing elements which may be serially connected so that collectively they produce a high voltage output.

Typically the current output of the generator will be such that the power rating of the generator is 100 mW or less, more usually 50 mW or less. For example, for a paint spraying device, the voltage may be in excess of 25 kV and the current of the order of 1 microamp (power rating of 30 mW) whilst for a room fragrance sprayer the voltage may be of the order of 0.5 to 2.0 mW, typically 1.2 mW (eg 100 nA current and 12 kV voltage).

The high voltage generator conveniently comprises an array of photosensitive elements so arranged as to produce a voltage output of at least 1 kV.

Preferably the array of photosensitive elements is so arranged as to produce a voltage output of at least 5 kV, and more preferably upwards of 8 kV.

The generator is conveniently in the form of an electronic solid state device comprising a large array of photosensitive elements. For instance, the solid state device may comprise a photovoltaic material (eg suitably doped polycrystalline silicon such as that used in the production of solar cells and solar panels) appropriately divided into discrete sections, eg by etching and/or laser scribing techniques commonly used in the production of semiconductor devices, to form a large array of discrete photovoltaic elements interconnected in such a way as to produce, collectively, a high voltage output of the order referred to above when irradiated.

A cell of photovoltaic material, such as silicon doped with boron to produce a pure lattice of p-type material, can produce a relatively low voltage output (typically of the order of 0.45 V) when illuminated depending on the light intensity and load, but independently of the surface area. Current output on the other hand is related to both light intensity and the surface area of the cell. For the kind of electrostatic spraying applications with which the present invention is primarily concerned, current demand is very low (microamps and even nanoamps) and consequently, by serially connecting a sufficiently large array of low voltage output photovoltaic elements consistent with the high voltage to be secured (eg several kV and greater), it is feasible to obtain sufficiently high voltages for electrostatic spraying applications without requiring the large surface areas usually associated with solar panels.

The voltage producing elements may be constituted by light sensitive elements, such as photovoltaic elements, connected in an array which is so disposed as to be irradiated by ambient light. In this case, the array may be located on an external part of the spraying device embodying the generator so as to be exposed to the surroundings. This embodiment may for instance find utility for room fragrance spraying since the generator may be active when the array is illuminated during daylight hours (and night time when the room lighting is switched on) but is deactivated during the hours of darkness when the room lighting is switched off.

Means may be provided for selectively exposing and shielding the array to/from ambient radiation/light according to whether high voltage output is required. For instance, the housing of the generator or spraying device may be provided with a sheath or other radiation shielding device movable between positions in which it conceals or exposes the array to the surroundings. The shield may alternatively be in the form of a removable cover which, when mounted on or attached to the generator or spraying device, prevents irradiation of the array, and allows irradiation when removed, the switching action thereby being effected by removal and replacement of the cover.

The shield/cover may be adjustable to vary the extent of exposure of the array and thereby vary the rate of spraying for instance.

Where the spraying device is designed for hand-held use, the device may comprise a portion intended to be held in the hand, eg a hand grip, and a section which would not normally be encompassed by the hand in use of the device, the array of photosensitive elements being disposed on the latter section so as to be exposed to ambient radiation/light.

When the array is arranged on a section of the device so as to be exposed in use, the array may be protected from damage by a superimposed layer or cover of material which is at least partially transmissive to the radiation/light.

In another embodiment, the voltage producing elements are constituted by radiation sensitive elements connected in an array arranged to be irradiated by a radiation source forming part of the spraying device. The radiation source may constitute the sole or primary source of radiation for the array or it may serve to supplement ambient radiation/light. For instance, the radiation source may be a radiation emitting element such as a light emitting solid state element (eg a light emitting diode), a filament (eg light bulb) which emits light when current is passed through the filament or a fluorescent lamp. Switching on and off of the generator in this instance may be controlled by switching the radiation emitting element on and off, in which case the switching device need only be a low voltage switch controlling a high voltage output. Alternatively switching on and off of the generator may be effected by means operable to expose and shield the array selectively to/from the radiation emitting element and such means may be movable by the user between exposure and shielding positions relative to the array.

Where the spraying device includes such a radiation source, the source may be connected to terminal means to which an electrical power source (such as a low voltage battery) is connectable. In this event, the housing of the spraying device preferably includes a compartment for insertion of the power supply and, if desired, the radiation source and the high voltage generator may be accommodated internally of the housing. Activation and deactivation of the generator may be effected by means of a user-controllable switch forming part of an electric circuit including the terminal means and the power supply (in use).

Exposure of the array (for example to control switching on and off of the generator) may be controlled by means of a user controllable actuator. In the case of a spraying device, the actuator may serve to control the supply of material to the outlet of the device and may also be coupled with a movable masking element so that, in response to delivery of the material to the spraying outlet, the array is exposed to produce high voltage for application to the material and thereby deliver a spray of electrically charged material. In a typical embodiment, the spraying device comprises a user operable trigger for applying pressure to electrostatically sprayable material contained in a reservoir or container (for example in the form of a piston and cylinder type device or in the form of a compressible container) to effect delivery of the material to the spraying outlet, and the trigger is coupled to a masking element which is moved relative to the array (translationally or rotationally) to expose or increase exposure of the array to ambient radiation or to radiation from an associated radiation source. Alternatively, the masking element may be omitted and the radiation source may be energised in response to actuation of the trigger whereby the array is irradiated in the course of operating the trigger to deliver the material to the spraying outlet.

If employed, the radiation source may serve a dual purpose, ie the production of light for irradiation of the photosensitive array, and for producing light for illumination of the object/target to be sprayed. In addition, the radiation source may serve to indicate that the generator is operational.

As disclosed in EP-A-468735 and 468736 and PCT-A-WO94/13063, it is desirable in some applications to provide a bipolar high voltage output, for example for the purposes of shock suppression and/or to allow the spraying of electrically insulating materials such as plastics, human hair etc, which are otherwise difficult to spray. The generator may for such applications be arranged to provide a bipolar output, eg with an output frequency as disclosed in EP-A-468735 and 468736. For example, the high voltage output of the generator may be electronically switched at a desired frequency (which may be user-controlled) by means of electrical circuitry associated with the generator to produce bipolar output, eg using high voltage switching arrangements as disclosed in PCT-A-WO94/13063. Alternatively the generator may comprise two arrays of photosensitive elements, the arrays being configured to produce respective positive and negative high voltage outputs and control means being provided to alternately irradiate the arrays (either by ambient radiation/light or by radiation/light produced by an associated radiation source or sources) so that the composite output alternates between positive and negative values at a frequency determined by the control means.

In a specific embodiment, a spraying device may comprise two high voltage generators of the solid state type disclosed above with radiation responsive switching means of the form disclosed in International Application No. WO94/13063 arranged to alternately switch the generators in such a way that a bipolar voltage is applied to the location or site from which a spray or a stream of ions is to be generated, positive voltage being derived from one generator and negative voltage from the other. For instance, each generator may be coupled to said location through a respective radiation responsive switching means and control circuitry may be provided to operate the switching means in alternating fashion with a predetermined periodicity by controlling the radiation sources associated with each switching means.

The material is preferably one which in bulk form, as a packed particulate mass, is not highly electrically insulating, typically exhibiting a resistivity of about $10^{11}$ ohm.cm or less, usually in the range of $10^5$ to $10^{11}$ ohm.cm so that the voltage can be applied to the particles at the surface through the mass of material.

For the avoidance of doubt, the volume resistivity of the material per se is not necessarily within the specified range. What is important is that the resistivity of the bulk powder should be appropriate to ensure that voltage applied to the bulk material is conducted to the surface from which the particles issue as a spray. Thus, for example, it is conceivable that the particles could be composed of a core of highly insulating material with a volume resistivity well in excess of $10^{11}$ ohm.cm but coated with a material of lower resistivity such that the particles exhibit a bulk resistivity within the range $10^5$ to $10^{11}$ ohm.cm when consolidated as a packed mass without compressing the packed mass. In some cases, the particulate material may comprise a mixture of materials having differing volume resistivities. For instance, where one material used alone is found not to spray satisfactorily, a mixture with a second material having a different volume resistivity may permit the combined materials to spray under the same voltage conditions.

Particles sprayable by methods in accordance with the present invention will usually have a mean particle size lying in the range of 1 to 1000 microns, typically less than 400 microns and preferably 10 to 200 microns. Preferably the particles are of a non-filamentary nature since elongate fibres or the like are more prone to corona discharge, with generally spherical particles being preferred.

Various applications of the method of the invention are envisaged, for example spraying of suitable powdered active ingredients for use in the following:

personal hygiene and care products such as deodorants, anti-perspirants, cosmetics (eg make up, talcs), medical and pseudo-medical formulations for application to the human body including, inter alia, nasal and oral cavities;

domestic products such as household cleaning and surface treatment materials (eg oven cleaners, kitchen utensils, bleaches, toilet powders), pesticides, insecticides, disinfectants, plant nutrients; and industrial products such as food additives, food coatings, utensil coating (eg baking tray coatings).

Thus, for example, some conventional anti-perspirants are based on an active material, such as aluminium compounds such as aluminium-chlorohydrate, in particulate form suspended in a volatile organic liquid vehicle to aid spraying. In accordance with the present invention only the anti-perspirant active ingredient (eg aluminium chlorohydrate) need be used in powder form. In this way, use of a volatile liquid vehicle can be eliminated.

In some applications of the invention, the arrangement may be such that the applied voltage is insufficient to cause issue or propulsion of particles from the bulk material until the electric field is sufficiently intensified, ie by bringing the mass of material into the proximity of an object or target towards which the particulate material is to be sprayed. In other words, the arrangement may be such that spraying of the particulate material is substantially suppressed until the surface from which the material issues is within a predetermined distance from the object or target to be sprayed. The distance involved may vary according to the particular application but for many applications the predetermined distance is typically about 25 cms or less. For some applications, said predetermined distance may be about 20 cms or less. In some cases, eg cosmetic applications and other applications involving spraying the body, said predetermined distance may be about 10 cms or less, and for applications requiring accurate directly spraying, it may be about 5 cms or less.

According to a further aspect of the invention there is provided a device for spraying particulate material, comprising a receptacle for the material to be sprayed, a voltage generator for applying high voltage to the mass of particulate material, and means defining a dispensing location from which electrically charged particles issue from the mass in use.

Preferably the material is sprayed from the device without effecting transport of the material with the aid of mobile gaseous fluid, the high voltage preferably being applied to the mass of the material while static within the containing receptacle.

Because the particles sprayed from the device are electrically charged, the spray will tend to be directional because of the earth seeking nature of a cloud of charged particles. In this way, formation of a "fog" of loose particles suspended in air is substantially avoided. Also, the particles by virtue of being electrically charged are less prone to being inhaled into the lungs. Moreover, because of the manner in which the particles are charged, ie by application of high voltage to the static mass accompanied by charge leakage through the mass, all of the particles will be charged whereas this is not necessarily the case where a corona discharge technique is used to charge a fluidised stream of particles as disclosed in International Patent Application No. WO94/19042.

Preferably the device is in the form of a self-contained unit comprising a housing which is suitable for hand-held use or is readily portable using one hand, the housing accommodating the high voltage generator and any power supply (eg a battery power supply) needed thereby.

The particulate material may be contained within a storage section within the housing of the device or it may be supplied by way of a replaceable and/or refillable container adapted for assembly with the device, eg insertion into a compartment within the housing of the device.

In one embodiment of the invention, the particulate material is accommodated within a reservoir or container (which may be replaceable) and the arrangement is such that, during spraying, a surface of the mass of particulate material is exposed whereby electrically charged particles issue from that surface via a discharge outlet of the device. Means may be provided for moving the mass of particulate material (either by displacement of the mass within the container or reservoir or by displacement of the container or receptacle) so as to compensate for the fall in the level of the mass as a result of spraying, ie so as adjust the level of said mass relative to the discharge outlet as the amount of particulate material reduces.

Preferably a user operable actuator is provided for controlling opening and closing of the discharge outlet through which the particulate material is discharged. The actuator may also control operation of the high voltage generator and the arrangement is conveniently such that operation of the actuator is effective to co-ordinate opening of the discharge opening with operation of the voltage generator.

The actuator may take various forms. For example, the particulate material-containing reservoir, container or the like may have an opening through which the powder exits and the actuator may comprise a movable element controlling opening and closing of the opening. The movable element may be in the form of a shutter (eg an iris-type shutter) or it may be formed with an aperture or apertures which can be moved into and out of registry with said opening in response to movement of the element. For example, the movable element may be slidable so that the aperture(s) therein are moved laterally relative to said opening between a position with the aperture(s) located in registry with said opening and a position in which the aperture(s) is/are displaced to one side of the opening and a non-perforated portion of the movable element overlies the opening thereby sealing the reservoir, container or the like, at least to the extent necessary to prevent escape of the particulate material. The sliding motion of the movable element may be rotary or translational with respect to the device. In a convenient arrangement, the movable element is arranged so that, when the device is held in the hand, it can be moved between its opening and closing positions by means of the user's thumb either by directly by sliding the thumb to and fro while in contact with the movable element or by while in contact with a part of the actuator linked with movable element controlling opening and closing.

If desired, the actuator may be biassed, eg spring loaded, towards the closing position, In other embodiments of the invention, the arrangement may be such that discrete quantities of the particulate material are made available for spraying. For example, operation of the device may involve separating a portion of the particulate material from the main bulk and the application of high voltage to the portion so separated.

Alternatively the particulate material may be stored as separate discrete quantities, for example in capsules or cells, and operation of the device may involve opening or rupturing the capsule or cell to expose the particulate mass therein with accompanying application of high voltage to the encapsulated mass to effect spraying. In this case, the particulate material may be encapsulated in a series of cells, eg coupled together in the form of a strip, and means may be provided for indexing the cells successively into a location at which each cell is opened or ruptured and at which the high voltage is applied to the mass of encapsulated material thus made available for spraying. The driving force for effecting indexing of the cells may be derived from effort imparted by the user, eg in moving a trigger or other user operable actuator which may also be arranged to render the high voltage generator operable in a manner co-ordinated with exposure of the particulate material.

The invention will now be described by way of example only with reference to the accompanying drawings, in which.

Figure 1:
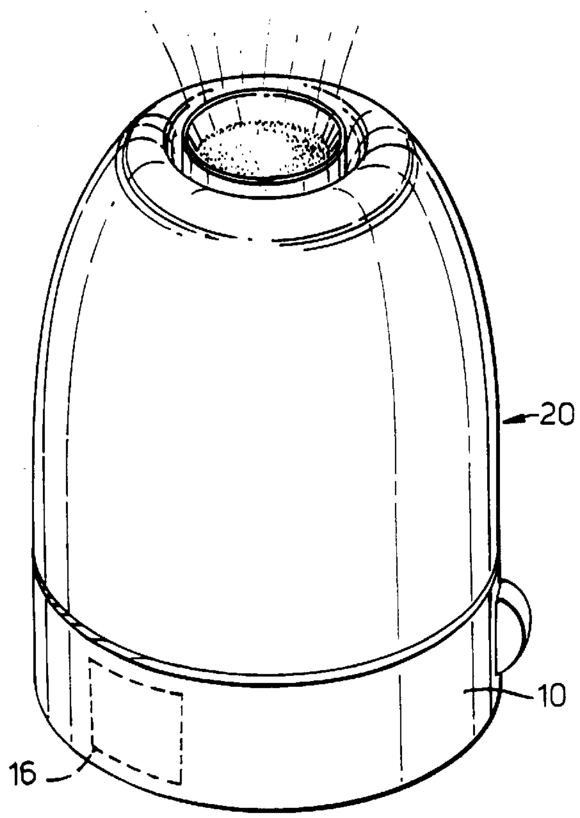
FIG. 1 is a diagrammatic view of a first embodiment for electrostatically spraying powder in a predominantly upward direction.
Figure 2:
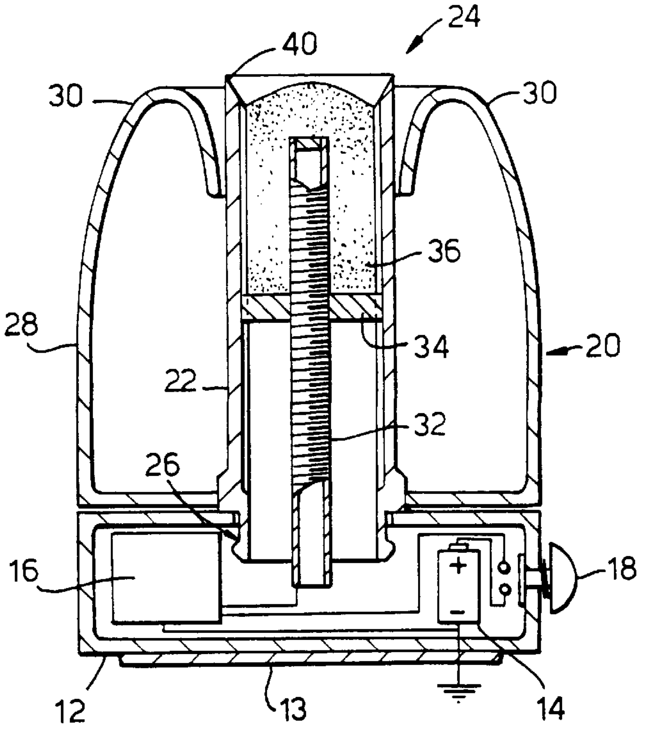
FIG. 2 is a vertical section through the device of FIG. 1.

Referring to FIGS. 1 and 2, the powder dispersing device illustrated comprises a base unit 10 for location on a horizontal surface, the bottom wall 12 of the base unit serving to provide a connection to earth via the surface on which it stands. For this purpose, the bottom wall 12 of the base unit includes a plate 13 of material which is electrically conductive or of material which has some degree of conductivity. The base unit 10 houses a low voltage battery supply 14 for powering circuitry 16 for producing a high voltage, typically of the order of 8 kV or more, under the control of a user operable switch 18. An upper unit 20 is mounted above the base unit 10 and comprises a central tubular portion 22, the upper end 24 of which is open and the lower end 26 of which is rotatably engaged in the base unit so that the upper unit 20 can be rotated about the axis of the tubular portion 22. The portion 22 is enclosed within an outer casing 28 which is contoured so as to provide an upwardly convex area 30 around the upper open end of the central tubular portion 22.

A fixed rod 32 is mounted on the base unit 10 and extends upwardly into the central tubular portion 22, the rod being externally threaded along its length and being engaged with a disc 34 which is mounted within the portion 22 and forms the base of a powder-receiving cavity 36. The disc 34 is provided with formations which are slidably engaged in longitudinal keyways in the inner peripheral wall of the portion 22 so that the disc is constrained against rotation relative to portion 22 but is free to move in the longitudinal direction in response to rotation of the upper unit 20 relative to the base unit 10. In this way, the depth of the powder-receiving cavity 26 can be varied as the quantity of powder in the cavity diminishes. As shown, the disc 34 is shown in an intermediate position along its range of travel.

In addition to co-operating with the disc 34, the rod 32 forms an electrically conductive path between a high voltage output (preferably positive) of the high voltage generating circuitry 16 and the interior of the powder-receiving cavity whereby high voltage can be applied to the powder in the cavity when the switch 18 is operated to energise the circuitry 16. In operation, by appropriate adjustment of the upper unit relative to the base unit, the exposed surface of the powder material can be maintained adjacent the open upper end of the tubular portion 22. The high voltage applied to the powder within the cavity 36 is conducted through the powder (which will be one which has at least some degree of conductivity to permit this) so that an electric field is produced whereby particles present at the exposed surface are propelled under the influence of the electric field away from the bulk of the powder. The upper edge 40 of the portion 22 is of tapering configuration to enhance the electric field intensity. A high voltage may be established at the upper edge either as a result of electrical charge accumulating on the edge (in the case where the tubular portion 22 is of highly insulating material) or by coupling the high voltage output of the circuitry 16 electrically to the edge, eg by means of a suitable conductive path via the rod 32 and the disc 34 and a conductive track extending along the tubular portion 22.

In order to retain the powder within the device when not in use, the upper unit 20 or the tubular portion 22 may be provided with a removable cover (not shown) providing a seal for the powder-receiving cavity 36.

Figure 3:
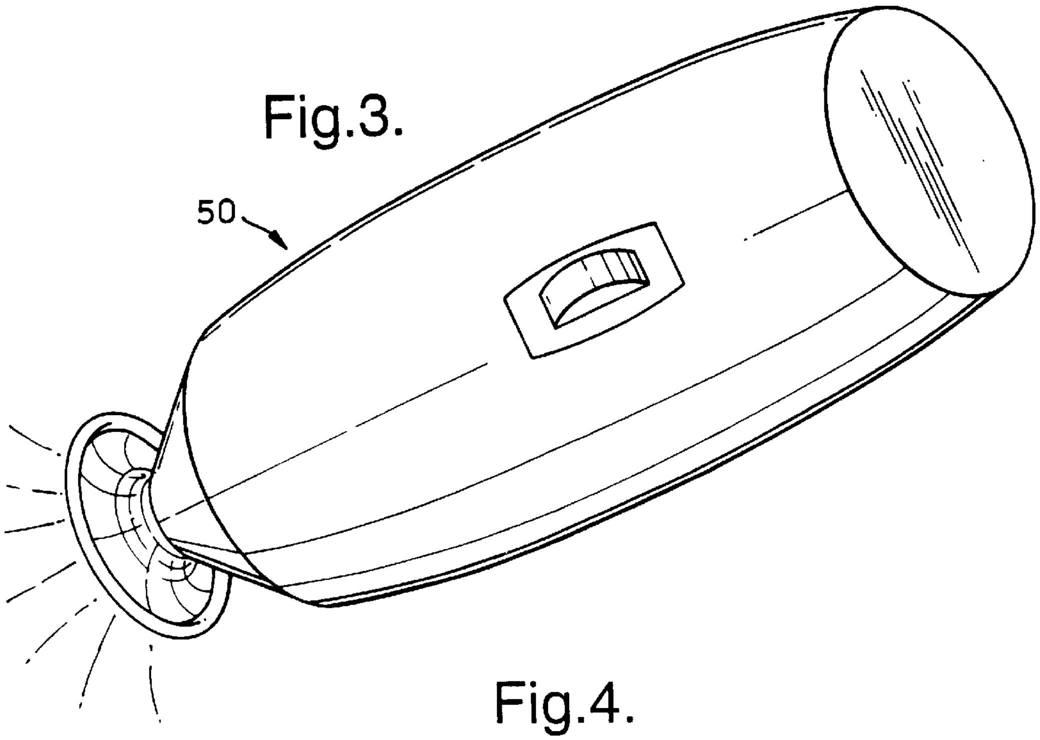
FIG. 3 is a diagrammatic view of a second embodiment which is designed for spraying powder in a predominantly downward direction.
Figure 4:
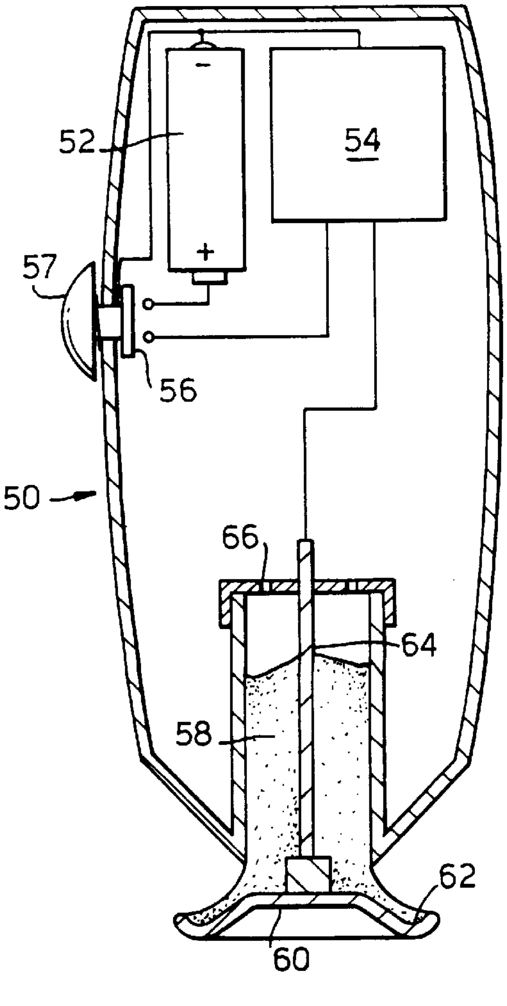
FIG. 4 is a vertical section through the device of FIG. 3.

Referring to FIGS. 3 and 4, the device comprises a housing 50 accommodating a dc battery supply 52 powering a high voltage generator 54 under the control of user operable switch 56. A connection to earth may be made via the user, ie by contact of the users finger with button 57 for actuating the switch 56. The housing 50 includes a powder-receiving cavity 58 with a shaped disc 60 mounted beneath the lower end of the cavity, the disc being formed with an annular channel 62 into which the powder can flow under gravity and being designed such that the angle of repose of the powder does not result in powder overflow. The high voltage output of the generator 54 is coupled to the interior of the cavity 58 and hence the powder contained therein by a rod 64 which may also serve to connect the disc 60 to the housing 50. Means (not shown) may be provided for moving or adjusting the position of the disc 60 relative to the housing for example to vary the size of the opening between the disc 60 and the lower end of the cavity 58 and/or to locate the disc 60 in a sealing position to prevent powder flow from the cavity 58 when the device is not in use. Such means may be co-ordinated with operation of the high voltage generator so that opening of the cavity is accompanied by the application of voltage to the powder, or vice versa. In operation, spraying is effected when the high voltage is applied to the powder with the disc in an extended position as shown so that the powder can flow into the channel 62, the voltage being conducted to the exposed surfaces of the mass of material resulting in the propulsion of particles of the material from such exposed surfaces. The upper end 66 of the cavity 58 is formed with one or more vents to allow the admission of air as the powder level falls. The illustrated device is intended primarily for lateral/download spraying of powder onto suitable surfaces.

Figure 5:
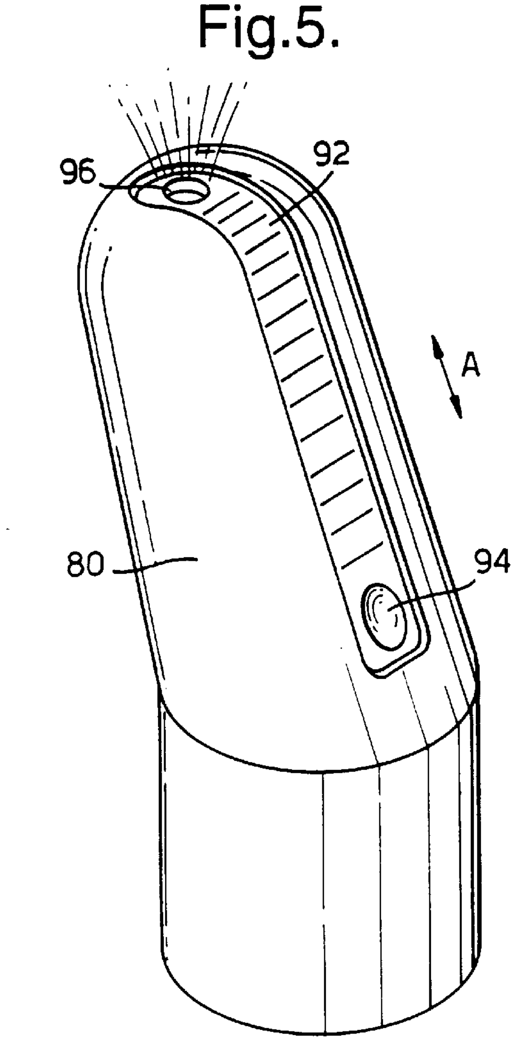
FIG. 5 is a diagrammatic view of a spraying device for use in the application of for example powdered personal care and hygiene products.
Figure 6:
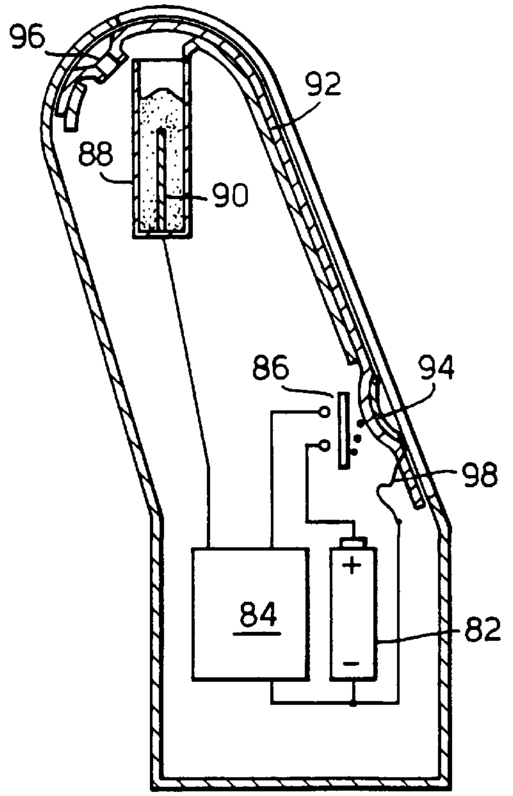
FIG. 6 is a vertical section through the device of FIG. 5.

Referring now to FIGS. 5 and 6, the device illustrated is suitable, inter alia, for spraying personal hygiene and care products. The housing 80 of the device accommodates a dc battery supply 82 powering a high voltage generator 84 under the control of user operable switch 86. The housing 80 includes a powder-receiving cavity 88 adjacent one end and voltage is applied to the interior of the cavity 88 via a conductor 90 connected to the high voltage output of the generator 84. The cavity 88 is open at its upper end but is sealed when not in use by slidable strip 92 of flexible material (eg a suitable plastics material).

The strip 92 extends down the side of the housing 80 and is formed with a notch 94 for registry with the thumb of the user. By appropriate manipulation with the thumb, the strip 92 can be moved relative to the open end of the cavity in the directions indicated by arrows A between a sealing position as shown in FIG. 6 and a spraying position as shown in FIG. 5 in which a hole 96 is brought into registry with the open end of the cavity to expose the powder. If desired, the actuating strip may be biassed, eg spring loaded, to the closed position shown in FIG. 6. The actuating strip 92 is coupled (shown diagrammatically) with the switch 85 in such a way that energisation and deactivation of the generator 84 is co-ordinated with opening and closing of the upper end of the cavity in response to manipulation of the strip 92. Thus, for example, the arrangement may be such that the generator 84 is not energised until the hole 96 is fully registered with the open end of the cavity. A conductive area 98 may be associated with the notch 94 so that earth connection for the electrical circuit is made when the user's thumb is registered with the notch. Where the device of FIGS. 5 and 6 is intended for use as an applicator for personal care and hygiene products, it will often be desirable to employ a voltage such that, with the generator energised and the powder exposed via hole 96, the electric field intensity does not become sufficient to initiate spraying of the powder until the upper end of the device is brought within a predetermined distance from the site to be sprayed, eg about 10 cms or less depending on the nature of the powder to be discharged: for instance, in the case of an eye shadow applicator the arrangement may be such that spraying is suppressed until the discharge outlet of the applicator is within say 1 cm of the site to be sprayed.

Figure 7:
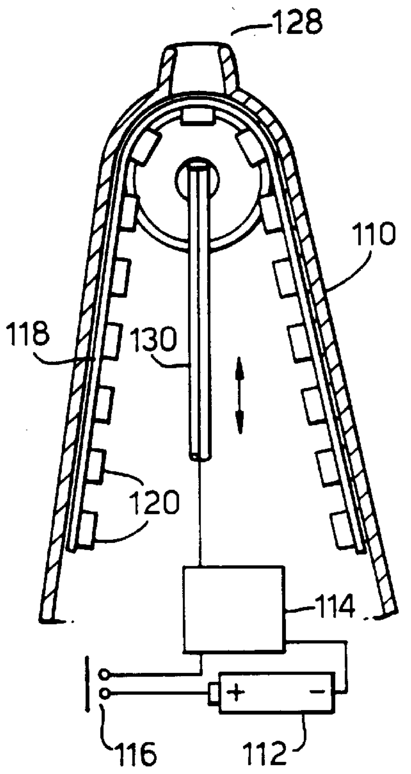
FIG. 7 is a diagrammatic view illustrating the principle of operation of another embodiment in accordance with the invention.
Figure 8:
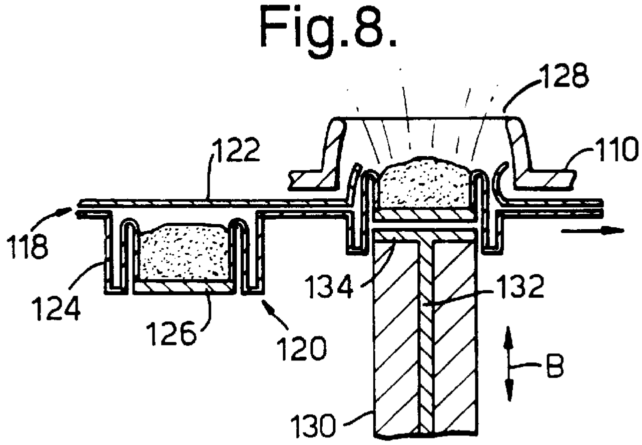
FIG. 8 is a detail view illustrating exposure of powder for spraying.

In the embodiments of FIG. 1 to 6, the powder is accomodated in a receptacle or cavity within the device. FIGS. 7 and 8 illustrate an alternative embodiment in which the powder to be sprayed is stored in capsule form, the capsule being ruptured to expose the powder when spraying is required. As in previous embodiments, the housing 110 (shown in part only) accomodates a dc battery supply 112 powering a high voltage generator 114 under the control of user operable switch 116. The housing 110 receives a strip 118 comprising a series of lengthwise spaced capsules 120 of powder. The strip comprises upper and lower layers 122, 124 of material such as foil between which discrete quantities of the powder material are encapsulated. The upper layer 122 at least is composed of a material which will readily rupture whilst the lower layer is composed of or includes at least in part material which is conductive or "semi-conductive" so that the high voltage can be applied to the powder within each capsule. In the illustrated embodiment, the lower layer 24 includes conductive sections 126 each in registry with respective capsules 120.

Means (not shown) is provided for feeding the strip 118 in stepwise fashion past an opening 128 so as to bring each capsule 120 in turn into registry with the opening 128. Aligned with the opening 128, there is a plunger 130 which has a central core 132 of conductive material connected to the high voltage output of the generator 114 and at its tip a conductive terminal portion 134 connected to the core so that the high voltage is conducted to the terminal portion 134. The plunger 130 is movable towards and away from the opening 128 (arrows B) and the path of travel (arrow C) of the strip 118 extends between the plunger tip and the opening 128 so that, when a capsule 120 is indexed into registry with the opening, movement of the plunger 130 makes contact between the terminal portion 134 and the section 126 and forces the capsule upwardly causing the upper layer of material to rupture thereby exposing the powder as shown in FIG. 8. By appropriately co-ordinating movement of the strip 120 and plunger 130 with energisation of the generator 114 (all of which may be effected in response to operation of an actuator coupled with the switch 116), exposure of the powder in the vicinity of the opening 128 is accompanied by application of high voltage to the powder via the core 132, terminal portion 134 and capsule section 126 with consequent spraying of a discrete amount of powder.

Figure 9:
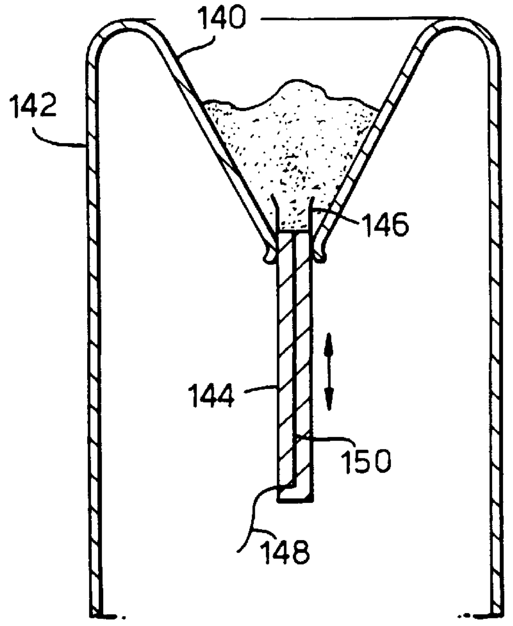
FIGS. 9 and 10 are diagrammatic views illustrating a further mode of operation.
Figure 10:
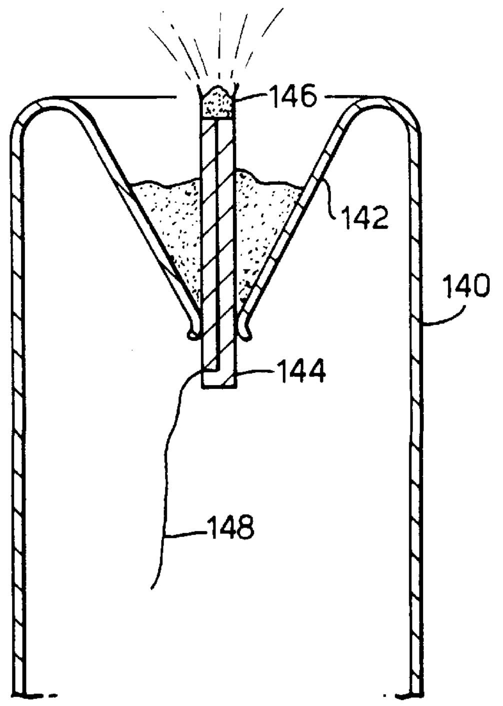

Referring next to FIGS. 9 and 10, in this embodiment discrete quantities (slugs) of powder are separated from a store within the device and high voltage is applied to the slugs. As shown schematically, the store of powder is in the form of a hopper section 140 associated with the housing 142. As in the embodiments described above, the housing accommodates a dc battery supply powering a high voltage generator under the control of user operable switch (not shown). A piston 144 extends through an opening at the base of the hopper section 140 and is slidably mounted within the housing for movement between a retracted position (FIG. 9) and an extended position (FIG. 10). Means (not shown) is provided for moving the piston to its extended position in response to operation of an actuator which is also coupled to the switch controlling operation of the generator. Such means may also control retraction of the piston or alternatively this may be effected automatically, eg by means of suitable biassing means, such as spring loading, on release of a user controlled actuator which may also control operation of the high voltage generator.

The upper end of the piston 144 mounts a cup 146 so that, as the piston moves from the retracted position to the extended position, it isolates a slug of the powder as shown in FIG. 10. The high voltage output of the generator is coupled to the powder contained within the cup 146 via lead 148 and conductive core 150 within the piston 144. Operation is co-ordinated so that the high voltage generator is energised when the piston has been extended to isolate a slug of the powder, which is then sprayed under the influence of the resulting electrostatic field. A cover (not shown) may be provided to seal the powder within the hopper section 140 when the device is not in use.

Figure 11:
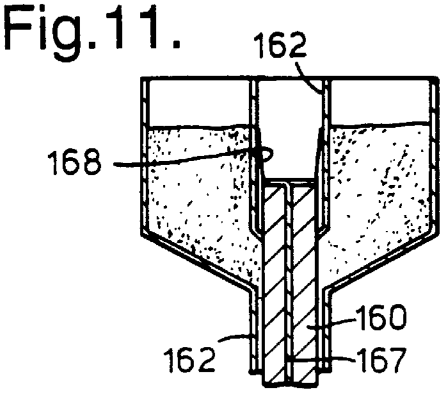
FIGS. 11 to 13 are diagrammatic views illustrating yet another mode of operation.
Figure 12:
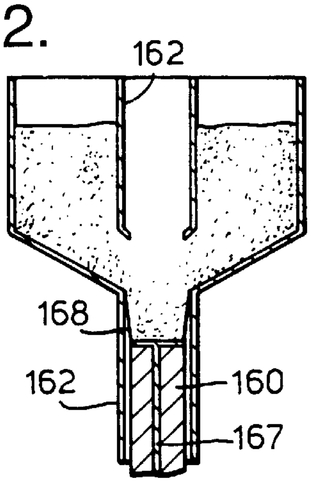
Figure 13:
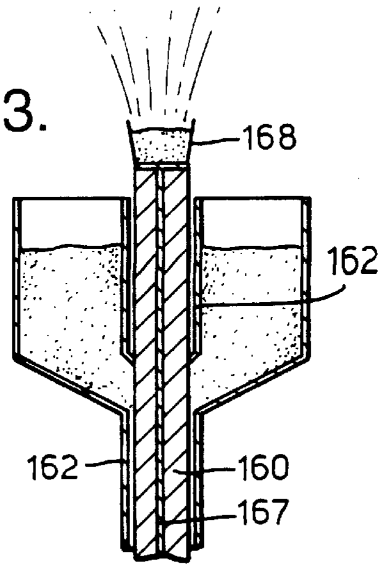

In a modification of the embodiment of FIGS. 9 and 10 (see FIGS. 11, 12 and 13), instead of the piston passing through the powder in order to collect a quantity thereof in the cup 146, the piston 160 may move within a bore 162 formed with a lateral opening 164 communicating with a store 166 of powder. When the device is not in use, the piston overlaps the opening 164 (see FIG. 11) and thereby prevents feed of powder into the bore 162. When the device is operated, a user operable drive mechanism (not shown) is effective to initially retract the piston (see FIG. 12) so that powder can enter the cup 168 at the leading end of the piston and then advance the piston to an extended position (FIG. 13). When the piston is in the latter position, high voltage is applied to the contents of the cup (via a conductor 167 passing through the piston) to effect spraying, operation of the high voltage generator being suitably co-ordinated with the drive mechanism. On completion of spraying the piston is returned to the position shown in FIG. 11.

Figure 14:
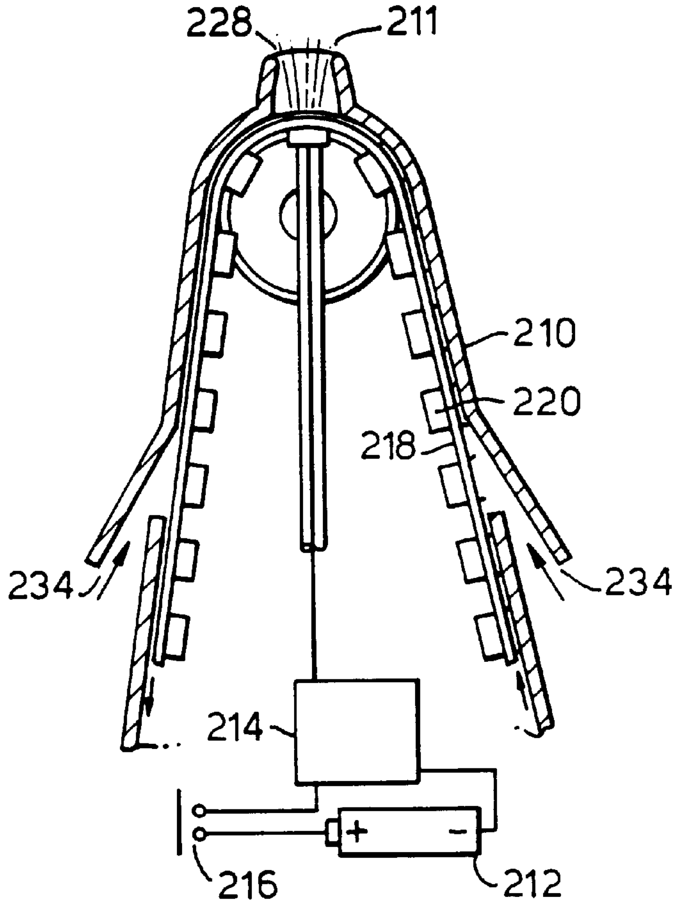
FIG. 14 is a diagrammatic view of a device suitable for spraying material for inhalation into the respiratory system.

FIG. 14 illustrates a device for spraying of medical pseudo-medical formulations in powder form into the respiratory tract. The powder to be sprayed is stored in capsule form, the capsule being ruptured to expose the powder when spraying is required. The housing 210 is designed so that its leading end 211 forms a nozzle portion suitably dimensioned for registry with the nostril or mouth (depending on whether it is to be used as a nasal or oral applicator). Openings 234 are provided in the housing to allow air to be drawn into the housing to the opening 228 when the user inhales. The housing 210 (shown in part only) accomodates a dc battery supply 212 powering a high voltage generator 214 under the control of user operable switch 216. The housing 210 receives a strip 218 comprising a series of lengthwise spaced capsules 220 of powder. The strip comprises upper and lower layers of material such as foil between which discrete quantities of the powder material are encapsulated. The upper layer at least is composed of a material which will readily rupture whilst the lower layer is composed of or includes at least in part material which is conductive or "semi-conductive" so that the high voltage can be applied to the powder within each capsule. In the illustrated embodiment, the lower layer includes conductive sections each in registry with respective capsules 220.

Means (not shown) is provided for feeding the strip 218 in stepwise fashion past an opening 228 so as to bring each capsule 220 in turn into registry with the opening 228. A mechanism (eg as shown in FIGS. 7 and 8) is provided for rupturing each capsule when it is aligned with the opening 228. By appropriately co-ordinating movement of the strip 220 and rupturing mechanism with energisation of the generator 214 (all of which may be effected in response to operation of an actuator coupled with the switch 216), exposure of the powder in the vicinity of the opening 228 is accompanied by application of high voltage to the powder with consequent spraying of a discrete amount of powder into the passageway in registry with the user's nose or mouth while the user inhales. In a modification, the device may include means for detecting the air flow created by inhalation on the part of the user and such means may be effective to initiate the above described operation in response to inhalation by the user.

In general, the dispensing outlet will be located upstream of the forward extremity of the nozzle portion in the direction of airstream flow induced by inhalation on the part of the user. As the spray is generated within the nozzle portion, at least a proportion of the electrically charged particles will have a tendency to deposit on to the nozzle portion as the latter will be at low potential when contacted with the user's nostril or lips. Deposition of particles on the nozzle portion can be much reduced by fabricating the nozzle portion from a good insulating material so that an electrical charge can build up on the nozzle surface during spraying thereby repelling deposition of charged particles on the surface.

In each of the embodiments described thus far, the voltage generator is powered by a low voltage source and serves to convert the low voltage into a low current, high voltage output. In each case, the high voltage generator may instead by a solid state voltage generating device which need not be powered by a separate power source. For example, the generator may comprise a large array of discrete voltage producing elements, eg photovoltaic elements, which are serially connected to produce a high voltage output in response to irradiation by light or other electromagnetic radiation such as infra-red. The array may be arranged so as to be exposed to ambient light, eg by locating it on an external surface of the device (e.g. as depicted by reference numeral 328 in the embodiment of FIG. 1) or by locating it internally adjacent an opening or window formed in the housing of the device. In this event, each of the devices illustrated may be provided with a movable cover which, when in place, shields the array and when removed or displaced from the shielding position allows exposure so that voltage generation is then possible.

Figure 15:
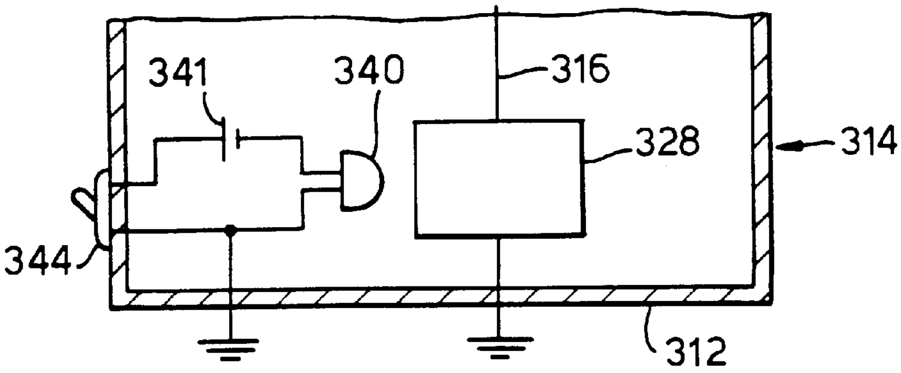
FIG. 15 illustrates schematically a modification which is applicable to each of the embodiments illustrated in FIGS. 1 to 14.

FIG. 15 shows an alternative arrangement which is applicable to each of the illustrated devices. In this arrangement, irradiation of the array forming the generator 328 is provided by a radiation producing device such as a light emitting diode (LED) 340 forming part of a low voltage circuit including user operable switch 344 and low voltage source 341, eg one or more low voltage batteries (which may be rechargeable). The low voltage circuit and the generator 328 have connections to earth through a wall 312 of the device housing 314. The connection to earth may be made by contact of that wall with an earthed surface on which the device is placed or by contact with the hand of a user. Closing and opening of the switch 344 is effective to energise and de-energise the LED 340 thereby controlling irradiation of the photovoltaic elements of the generator 328. Thus, closure of the switch serves to irradiate the generator and produce a low current, high voltage output, typically of the order of 5 to 15 kV, and in use this voltage is applied via lead 316 to the mass of particulate material to effect electrostatic spraying thereof. If necessary, an optical device such as a lens may be associated with the LED 340 to ensure that the radiation emitted is uniformly distributed over the array of voltage producing elements.

In each of the embodiments described with reference to the drawings, it will be understood that the arrangement be may such that spraying is suppressed until the device is brought into appropriate proximity with the target to be sprayed. The extent of proximity appropriate will tend to vary for different applications. For instance, if the device is intended for use a cosmetic applicator the degree of proximity will tend to be closer than a device intended for use in the application of domestic cleaning agents. Proximity control may for instance be provided by means of a cylindrical shroud (or other potential gradient attenuating means) encircling the zone from which the powder is to be sprayed and carrying a voltage such that the local potential gradient is attenuated, at least until the device is brought into close proximity with the target to be sprayed at which time the close proximity of the low potential target (eg at earth potential) will serve to intensify the electric field local to the exposed surface of the power mass and permit the commencement of spraying. The voltage established on the shroud may be produced by stray corona discharge generated by the high potential present or it may be positively applied by connecting the shroud to the high voltage generator in any convenient manner. Proximity control may alternatively or additionally be effected by appropriate selection of the voltage applied to the powder, ie insufficient to develop a spray until the device is brought close to a low potential target.

One application where proximity control can be advantageous is in the spraying of insecticides. In such an application, the device may be arranged so that spraying is suppressed normally but is initiated in the event of an insect such as a housefly passing close to the location at which the spray issues, the presence of the insect being effective to intensify the electric field and cause discharge of powder which will be attracted to the insect. The device may be provided with means for attracting insects, eg the powder may be one which, in addition, to acting as an insecticide produces a scent or smell effective to attract insects or the device may be arranged to emit radiation to attract insects, eg in the dark.

In experimental work, we have been found that a variety of materials such as silica gel crystals, aluminum chlorohydrate particles, brown sugar and white sugar, can be made to spray satisfactorily. More specifically, satisfactory spraying has been achieved using:

Merck Silica Gel 60 in the following size ranges
- 0.015 to 0.04 mm (Product No. 15111)
- 0.04 to 0.063 mm (Product No. 9385)
- 0.063 to 0.2 mm (Product No. 7734)
- 0.2 to 0.5 mm (Product No. 7733)

and

Macrospherical 95 aluminium chlorohydrate supplied by Reheis Inc. 235 Snyder Avenue, Berkeley Heights, N.J. 07922, USA In an experiment designed to explore proximity control, a cylindrical cup composed of Delrin (height 58 mm, inside diameter 38 mm and outside diameter 44 mm) was fitted internally with an electrode at the base thereof and was mounted with the longitudinal axis of the cup vertical and its open mouth presented upwardly. The electrode was connected, by means of an HT cable, to the output of a high voltage generator (Applied Kilovolts KS 30/26P). The cup was then filled with various samples of silica gel particles (as specified above) and a high voltage was applied to the electrode. Successful spraying of the powders was obtained by adjusting the voltage. The voltage was then adjusted until a condition was obtained where the voltage was below the threshold at which particles were observed, with the aid of backlighting, to be propelled from the cup. Under these conditions, it was found that if an object is brought into the vicinity of the open mouth of the cup, the presence of the object if sufficiently close was effective to induce spraying (ie as a result of the electric field being intensified by the introduction of a proximate object at low potential).

Figure 16:
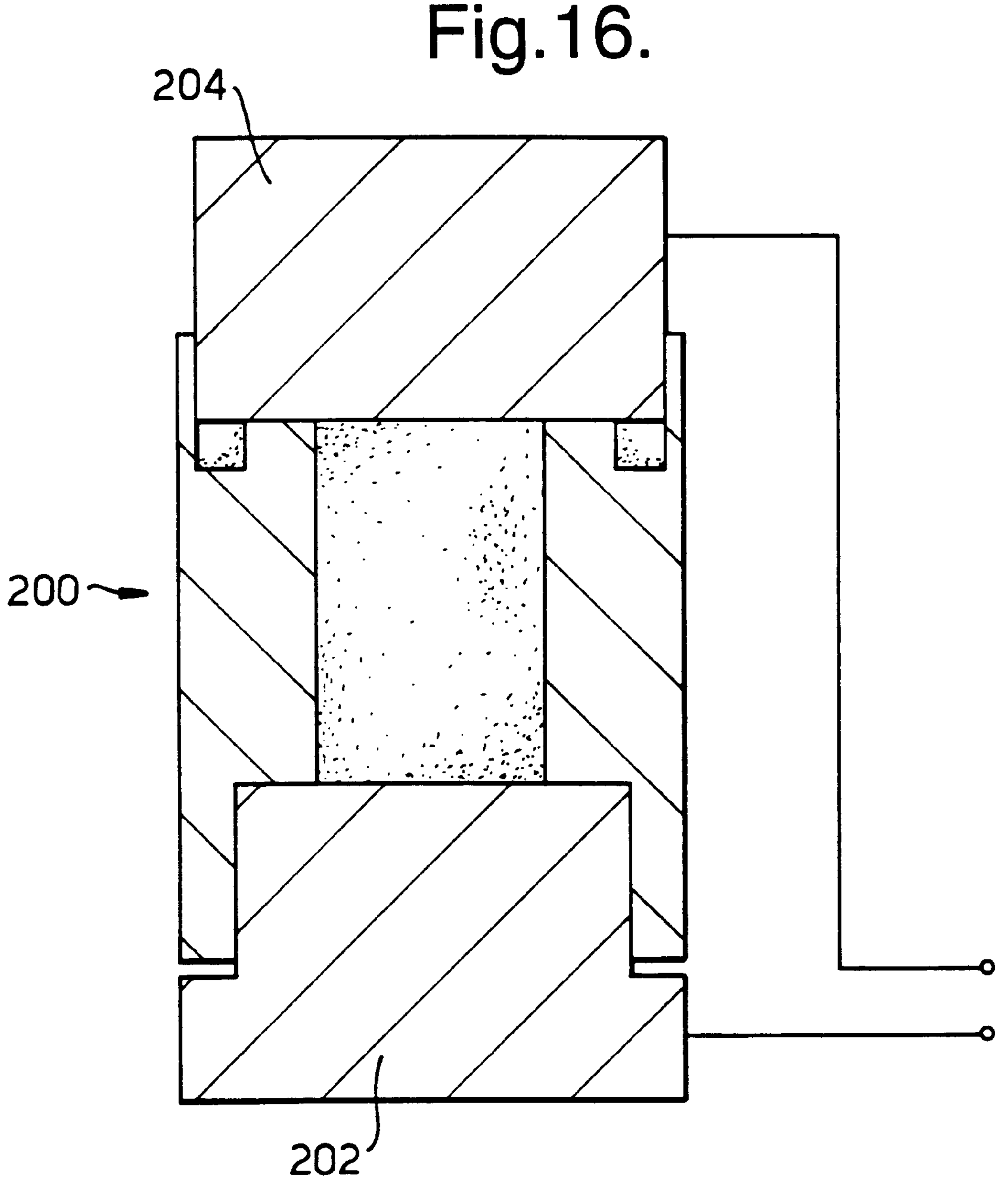
FIG. 16 is a schematic view of a cell for use in determining bulk powder resistivity.

Experimental work also indicates that powders that produce poor quality spraying when used alone can be made to spray more effectively when mixed with a powder having better spraying qualities. Thus, for example, a pure aluminium chlorohydrate grade (Micro-dry, available from Reheis Inc) having a resistivity of about $1.3\times10^{6}$ measured by the technique described below with reference to FIG. 16, was found to spray poorly even when brought close to earth and tended to be dispensed as large aggregates. However, when mixed with silica gel powder (size range 15 to 40 microns), eg. in a w/w ratio of 75% aluminium chlorohydrate: 25% silica gel, the mixture was found to produce a fine even spray. The resistivity of the mixture was measured as $2.4\times10^7$ ohm.cm using the method described below.

As mentioned previously, resistivities as referred to in the context of the present invention relate to the resistivity of the packed particulate material, ie bulk powder resistivity, as opposed to the volume resistivity of the material per se. The bulk powder resistivity may be measured in the following manner, using a powder-receiving cell as shown in FIG. 14. The cell 200 is generally cylindrical and is closed at each end by an electrode 202, 204 by means of which the cell, filled with powder, can be connected across an AC bridge such as a Wayne-Kerr Automatic Precision Bridge B905, obtainable from Farnell Instruments, Durban Road, Bognor Regis, West Sussex, England. With one of the electrodes removed, the cell is loosely filled with the powder and then repeatedly tapped on a surface to aid consolidation of the powder under gravity. When settling of the powder is observed to have ceased, the mass of powder in the cell is topped up until slightly proud of the powder containing cavity, the surplus is removed (eg by using a sheet of paper as a doctor blade) and the cell is closed by replacing the electrode. The resistance of the powder enclosed between the electrodes is then measured using the AC bridge and the measured value is converted to a bulk powder resistivity, $\rho_P$, using the standard formula:

$$\rho_P=RI/A$$

where R is the measured resistance (ohms), I is the axial length (cm) of the plug of powder in the cell and A is the cross-sectional area of the powder plug ($cm^2$).

What is claimed is:

1. A device for spraying particulate material, said device being in the form of a self-contained unit comprising a housing which is suitable for hand-held use or is readily portable using one hand, and including a receptacle for a mass of particulate material to be sprayed, a voltage generator for applying high voltage to said mass of particulate material, said voltage generator having an output with a power rating no greater than 100 mW such that, in the absence of said mass of particulate material, substantially no corona discharge occurs when said voltage generator is operative, and means defining a dispensing location at which, during spraying operation of said device, a surface of said mass of particulate material is exposed and from which surface, in use, electrically charged particles issue from said mass of particulate material and are discharged through a dispensing outlet.

2. A device as claimed in claim 1 including a user operable actuator for controlling opening and closing of said dispensing outlet.

3. A device as claimed in claim 1 including a holder for locating a discrete quantity of said mass of particulate material in the vicinity of said dispensing location.

4. A device as claimed in claim 1 including means for storing said mass of particulate material as separate discrete quantities, means for locating each such discrete quantity at said dispensing location and means for applying said high voltage to each such discrete quantity when individually registered in turn with said dispensing location.

5. A device as claimed in claim 1 in which said means defining said dispensing location is operable to separate a portion of said mass of particulate material from the main bulk of said mass of particulate material stored in said device and said voltage generator is arranged to supply said high voltage to the portion so separated.

6. A device as claimed in claim 1 in which said dispensing location in use is unscreened.

7. A device as claimed in claim 1 in which the output voltage of said voltage generator is no greater than 25 kV.

8. A device as claimed in claim 1 including a nozzle portion which is suitable for registry with a nasal or oral cavity of a user.

9. A device as claimed in claim 8 in which said nozzle portion defines a passageway through which, in use, air can be drawn by inhalation on the part of a user, said nozzle portion being associated with said dispensing location so that the material is dispensed into said passageway whereby, with the assistance of user-induced air flow through said passageway, the particles pass through said nozzle portion into a nasal or oral cavity of a user.

10. A device as claimed in claim 9 in which said dispensing outlet is located upstream of a forward extremity of said nozzle portion.

11. A device as claimed in claim 1 in which said voltage generator provides a bipolar output.

12. A device as claimed in claim 1 in which said receptacle is in the form of a replaceable cartridge comprising a container, said mass of particulate material being in said container, said container having an opening at which a surface of said mass of particulate material is exposed in use, and means for conducting high voltage from a source external to said container to said mass of particulate material therein whereby, in use, high voltage is conducted through said mass of particulate material to said exposed surface with consequent projection of particles from said surface.

13. A device for spraying particulate material, said device being in the form of a self-contained unit comprising a housing which is suitable for hand-held use or is readily portable using one hand, and including a receptacle for a mass of particulate material to be sprayed, a voltage generator for applying high voltage to said mass of particulate material, means defining a dispensing location at which, during spraying operation of said device, a surface of said mass of particulate material is exposed and from which surface, in use, electrically charged particles issue from said mass of particulate material and are discharged through a dispensing outlet, means for storing said mass of particulate material as separate discrete quantities, means for locating each such discrete quantity at said dispensing location and means for applying said high voltage to each such discrete quantity when individually registered in turn with said dispensing location.

14. A device as claimed in claim 13 in which said discrete quantities of material are encapsulated by an encapsulating material and means is provided for opening or rupturing said encapsulating material at said dispensing location to expose said discrete quantity therein with accompanying application of high voltage to said discrete quantity to effect spraying.

15. A device as claimed in claim 14 in which said discrete quantities of particulate material are encapsulated in a series of cells coupled together and means is provided for indexing said cells successively into said dispensing location at which each cell is opened or ruptured and at which said high voltage is applied to each discrete quantity thus made available for spraying.

16. A device for spraying particulate material, said device being in the form of a self-contained unit comprising a housing which is suitable for hand-held use or is readily portable using one hand, and including a receptacle for a mass of particulate material to be sprayed, a voltage generator for applying high voltage to said mass of particulate material, and means defining a dispensing location at which, during spraying operation of said device, a surface of said mass of particulate material is exposed and from which surface, in use, electrically charged particles issue from said mass of particulate material and are discharged through a dispensing outlet, said means defining said location being operable to separate a portion of said mass of particulate material from the main bulk of said mass of particulate material stored in said device and said high voltage generator being arranged to supply said high voltage to said portion so separated.

* * * * *